United States Patent
Pietri et al.

(10) Patent No.: US 11,588,495 B2
(45) Date of Patent: Feb. 21, 2023

(54) ANALOG FRONT-END CIRCUIT CAPABLE OF USE IN A SENSOR SYSTEM

(71) Applicant: NXP USA, Inc., Austin, TX (US)

(72) Inventors: Stefano Pietri, Austin, TX (US); Michael Todd Berens, Austin, TX (US); Yikun Mo, Suzhou (CN); Ashutosh Jain, Austin, TX (US)

(73) Assignee: NXP USA, Inc., Austin, TX (US)

( * ) Notice: Subject to any disclaimer, the term of this patent is extended or adjusted under 35 U.S.C. 154(b) by 0 days.

(21) Appl. No.: 17/305,627

(22) Filed: Jul. 12, 2021

(65) Prior Publication Data

US 2022/0052707 A1    Feb. 17, 2022

(30) Foreign Application Priority Data

Aug. 14, 2020    (CN) .......................... 202010822640.6

(51) Int. Cl.
    *H03M 1/00*    (2006.01)
    *H03M 3/00*    (2006.01)
    *A61B 5/00*    (2006.01)

(52) U.S. Cl.
    CPC ........... *H03M 3/496* (2013.01); *A61B 5/7225* (2013.01)

(58) Field of Classification Search
    CPC ........ H03M 3/496; H03M 3/45; H03M 3/454; H03M 3/458; H03M 3/494; H03M 3/422; H03M 3/462; H03M 3/464; A61B 5/7225
    USPC ....................................................... 341/122
    See application file for complete search history.

(56) References Cited

U.S. PATENT DOCUMENTS

| | | | | |
|---|---|---|---|---|
| 6,956,519 B1* | 10/2005 | Huang | ................ | H03M 1/0863 |
| | | | | 341/172 |
| 7,034,737 B1* | 4/2006 | Huang | ................. | H03M 1/147 |
| | | | | 341/172 |
| 7,920,085 B2* | 4/2011 | Lin | ..................... | H03M 1/1014 |
| | | | | 341/172 |
| 8,537,046 B2* | 9/2013 | Zhao | ................... | H03M 1/0604 |
| | | | | 341/172 |
| 8,711,024 B2* | 4/2014 | Sabut | ..................... | H03F 3/005 |
| | | | | 341/155 |
| 9,019,140 B2* | 4/2015 | Zhao | ....................... | H03M 1/06 |
| | | | | 341/172 |
| 9,319,033 B1* | 4/2016 | Jin | ......................... | H03K 4/502 |
| 9,525,426 B2* | 12/2016 | Stojanovic | ........... | H03M 3/458 |

(Continued)

OTHER PUBLICATIONS

Wang et al.: "A 19 nV/√ Hz Noise 2- μV Offset 75- μA Capacitive-Gain Amplifier With Switched-Capacitor ADC Driving Capability", IEEE Journal of Solid-State Circuits, vol. 52, No. 12, Dec. 2017, pp. 3194-3203.

*Primary Examiner* — Jean B Jeanglaude

(57) ABSTRACT

During a sampling phase, an analog front end circuit connects input of a first sampling capacitor to an analog input signal and input of a second sampling capacitor to a reference signal, and connects first and second hold capacitors to ground. During a partial tracking phase, input of the first sampling capacitor is connected to the reference voltage and the input of the second sampling capacitor is connected to the analog input signal. The first hold capacitor is connected to a first output of a gain amplifier and the second hold capacitor to a second output of the gain amplifier. Output of the first sampling capacitor is coupled to a first input of an amplifier and output of the second sampling capacitor is coupled to a second input of the amplifier.

20 Claims, 5 Drawing Sheets

(56) References Cited

U.S. PATENT DOCUMENTS

| | | | | |
|---|---|---|---|---|
| 9,748,969 B1* | 8/2017 | Bach | .................... | H03M 3/496 |
| 10,826,523 B2* | 11/2020 | Adusumalli | ......... | G01R 31/382 |
| 2004/0263376 A1* | 12/2004 | Shimizu | ................ | H03M 1/142 |
| | | | | 341/172 |
| 2013/0050003 A1* | 2/2013 | Wang | .................... | H03M 3/342 |
| | | | | 341/172 |

* cited by examiner

ANALOG FRONT-END CIRCUIT CAPABLE OF USE IN A SENSOR SYSTEM

CROSS-REFERENCE TO RELATED APPLICATIONS

This application claims the priority under 35 U.S.C. § 119 of China application no. 202010822640.6, filed on 14 Aug. 2020, the contents of which are incorporated by reference herein.

BACKGROUND

Field

This disclosure relates generally to integrated circuits, and more specifically, to an analog front end circuit.

Related Art

Analog front-end circuits are commonly used in integrated circuits (ICs) to receive analog signals and convert them to a digital input for use within the IC. An analog front-end circuit typically includes an amplifier and an analog-to-digital converter (ADC). These analog front-end circuits may be used, for example, for biomedical applications or audio applications, in which the analog front-end circuit can convert a low frequency and low amplitude signal to a high resolution digital signal. These type of analog front-end circuits are also commonly used for portable battery-operated devices. Therefore, a need exists for such analog front-end circuits with reduced cost (e.g. area) and reduced power consumption, while still preserving accuracy of the analog front-end.

BRIEF DESCRIPTION OF THE DRAWINGS

The present invention is illustrated by way of example and is not limited by the accompanying figures, in which like references indicate similar elements. Elements in the figures are illustrated for simplicity and clarity and have not necessarily been drawn to scale.

DETAILED DESCRIPTION

In one aspect, an analog front-end circuit of an IC includes a programmable gain amplifier (PGA) and analog-to-digital converter (ADC) circuitry in which the PGA samples at a lower rate than the ADC. This results in a reduction in both power and size of the operational amplifier of the PGA. Furthermore, the PGA uses sample and partial tracking phases (as opposed to sample and hold phases or sample and track phases) which allows for a reduction in size of the sampling capacitor and power of the PGA for a given PGA noise level. However, the sample and partial tracking introduces distortion at the higher frequencies. Therefore, through the use of ADC circuitry with filtering (either through the use of a sigma-delta (SD) ADC or a low pass filter with any type of ADC), the introduced distortion and noise is filtered out by the ADC circuitry. In this manner, a smaller PGA can be implemented while still maintaining an accurate ADC conversion.

Figure 1:
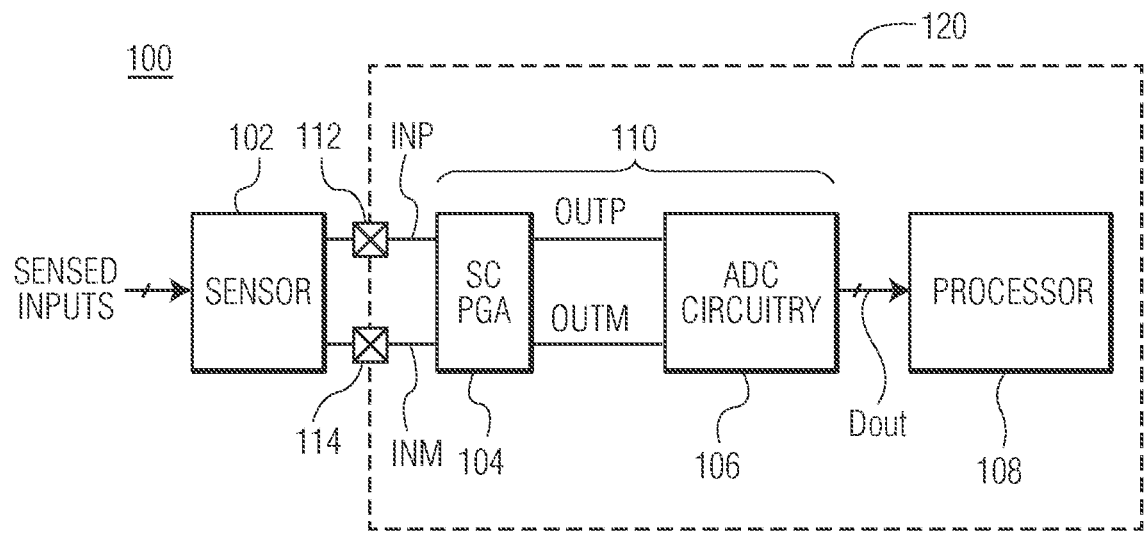
FIG. 1 illustrates, in block diagram form, a system including a sensor coupled to an integrated circuit (IC) having an analog front-end circuit, in accordance with one embodiment of the present invention.

FIG. 1 illustrates, in block diagram form, a sensor system 100 including a sensor 102 coupled to an IC 120. In the illustrated embodiment, sensor 102 is illustrated as being located external to IC 120, but alternatively, may be located within IC 120. In one embodiment, sensor 102 is a medical sensor, such as, for example, a heartbeat monitor. Sensor 102 is coupled to receive sensed inputs and coupled to provide sensor outputs to SC PGA 104 (also referred to herein as PGA 104) via terminals 112 and 114. In many applications, sensor outputs provide low frequency and low amplitude signals. A first input of PGA 104, referred to as INP, is coupled to terminal 112 and a second input of PGA 104, referred to as INM, is coupled to terminal 114. INP and INM correspond to a differential input to PGA 104. PGA 104 provides an amplified analog differential output, signals OUTP and OUTM, which are provided as a differential input to ADC circuitry 106. ADC circuitry 106 converts the analog differential input to a digital data stream output, Dout, which is provided to a processor 108 for further processing. PGA 104 and ADC circuitry 106 form an analog front-end circuit 110 of IC 120. In the illustrated embodiment, processor 108 can be any type of data processor.

In one embodiment, sensor 102 provides an analog differential signal via terminals 112 and 114 to PGA 104 as INP and INM, respectively. Alternatively, sensor 102 may be coupled to provide a single ended analog signal to one of terminals 112 or 114, while the other one of terminals 112 or 114 may receive a reference voltage or may be coupled to a voltage supply terminal, such as a VDD or VSS. Therefore, INP and INM can be referred to, together, as a differential signal, or one of INP or INM may be referred to as an input analog signal and the other of INP or INM a may be referred to as a reference signal.

Figure 4:
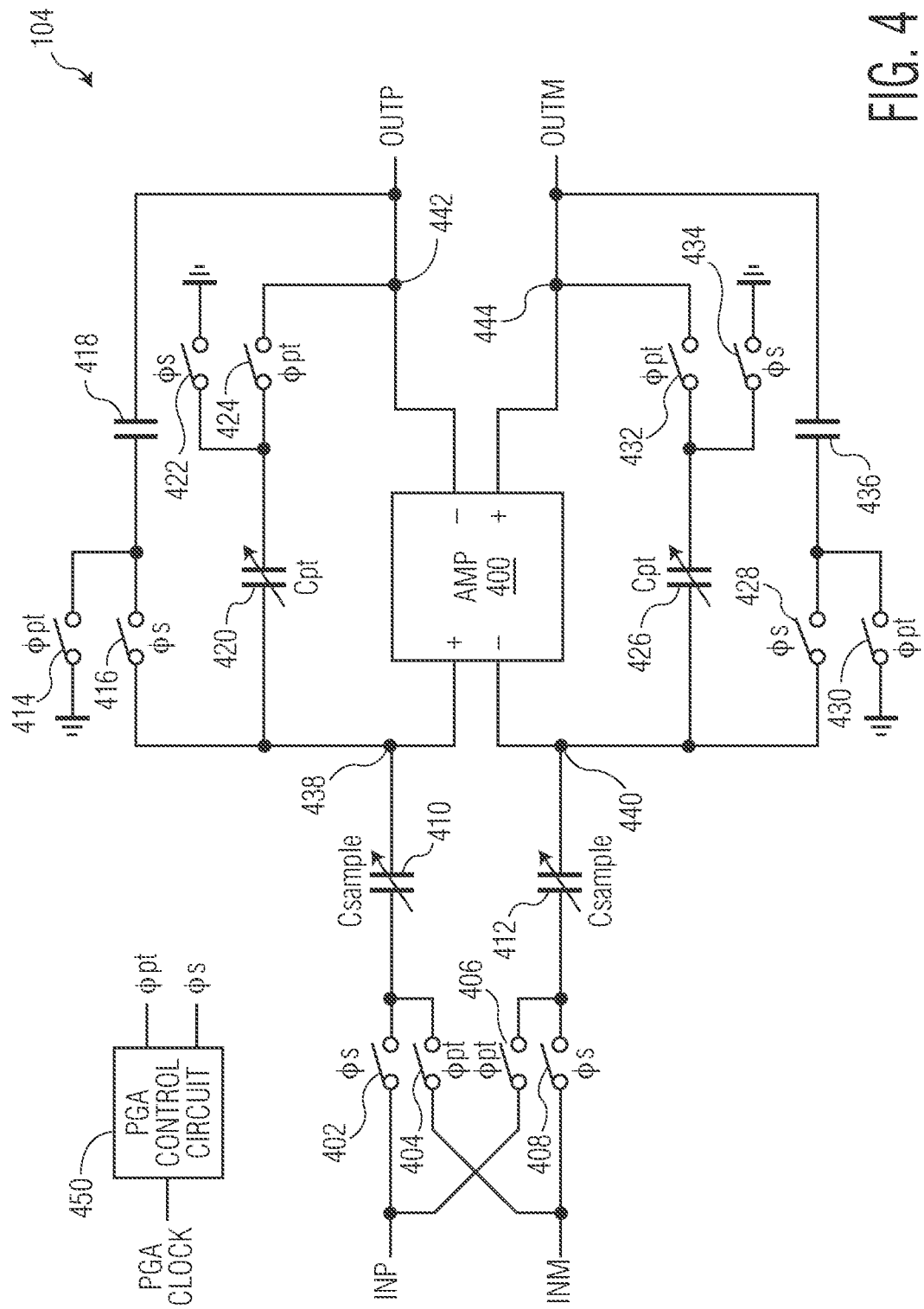
FIG. 4 illustrates, in partial schematic and partial block diagram form, a more detailed view of the switched capacitor programmable gain amplifier (SC PGA) of FIG. 1, in accordance with one embodiment of the present invention.

FIG. 4 illustrates, in partial block diagram and partial schematic form, PGA 104 in accordance with one embodiment of the present invention. PGA 104 includes an amplifier 400, sample capacitors $C_{sample}$ 410 and $C_{sample}$ 412, partial tracking capacitors $C_{pt}$ 420 and $C_{pt}$ 426, capacitors 418 and 436, PGA control circuit 450, and switches 402, 404, 406, 408, 414, 416, 422, 424, 432, 434, 428, and 430. PGA control circuit 450 receives a PGA clock signal, and based on the PGA clock signal, provides control signals ϕpt and ϕs. Assertion of ϕs corresponds to the sampling phase of PGA 104 and assertion of ϕpt corresponds to the partial tracking phase of PGA 104. Each switch in PGA 104 receives one of ϕs or ϕpt at its control input, in which assertion of the received control signal closes the corresponding switch such that it is conductive between its two data terminals and negation of the control signal opens the corresponding switch such that it is not conductive between its two data terminals.

INP is provided to a first input of PGA 104 and INM to a second input of PGA 104. The first input is coupled to a first data terminal of switch 402 and a first data terminal of switch 406. The second input is coupled to a first data terminal of switch 404 and a first data terminal of switch 408. A second data terminal of switch 402 and a second data terminal of switch 404 are coupled to a first terminal of $C_{sample}$ 410. A second data terminal of switch 406 and a second data terminal of switch 408 are coupled to a first terminal of $C_{sample}$ 412. Switches 402 and 408 receive φs at their control inputs, and switches 404 and 406 receive φpt at their control inputs. A second terminal of $C_{sample}$ 410 is coupled to a circuit node 438 at a first input (e.g. a non-inverting input) of amplifier 400, and a second terminal of $C_{sample}$ 412 is coupled to a circuit node 440 at a second input (e.g. inverting input) of amplifier 400. A circuit node 442 at a first output (e.g. inverting output) of amplifier 400 provides a first output of PGA 104, OUTP. A circuit node 444 at a second output (e.g. non-inverting output) of amplifier 400 provides a second output of PGA 104, OUTM. Amplifier 400 can be implemented as an operational amplifier (Opamp).

Still referring to FIG. 4, circuit node 438 is coupled to a first data terminal of switch 416 and to a first terminal of $C_{pt}$ 420. Circuit node 440 is coupled to a first data terminal of switch 428 and to a first terminal of $C_{pt}$ 426. A second data terminal of switch 416 is coupled to a first data terminal of switch 414 and a first terminal of capacitor 418. A second data terminal of switch 414 is coupled to ground. A control input of switch 414 is coupled to receive φpt and a control input of switch 416 is coupled to receive φs. A second data terminal of switch 428 is coupled to a first data terminal of switch 430 and a first terminal of capacitor 436. A second data terminal of switch 430 is coupled to ground. A control input of switch 430 is coupled to receive φpt and a control input of switch 428 is coupled to receive φs. A second terminal of capacitor 418 is coupled to circuit node 442. A second terminal of $C_{pt}$ 420 is coupled to a first data terminal of switch 422 and a first data terminal of switch 424. A second data terminal of switch 422 is coupled to ground, and a second data terminal of switch 424 is coupled to circuit node 442. A second terminal of capacitor 436 is coupled to circuit node 444. A second terminal of $C_{pt}$ 426 is coupled to a first data terminal of switch 434 and a first data terminal of switch 432. A second data terminal of switch 434 is coupled to ground, and a second data terminal of switch 432 is coupled to circuit node 444. Note that the second data terminal of each of switches 414 and 430 is coupled to ground. In one embodiment, this ground may be an analog ground, i.e. a stable voltage between a positive power supply and negative power supply used as reference voltages for analog circuits. Alternatively, this ground can be a positive power supply, negative power supply, or common ground.

In operation, PGA 104 is a switched capacitor PGA (SC PGA) which amplifies the input signal and whose gain is digitally programmable. In the illustrated embodiment, PGA 104 utilizes correlated double sampling (CDS) together with a double-sampling scheme which operates in two phases: the sample phase (corresponding to φs) and the partial tracking phase (corresponding to φpt). Note that φs is asserted during the sample phase and φpt is asserted during the partial tracking phase, so only one of φs and φpt is asserted at any one time. In one embodiment, φs and φpt may be referred to as clock signals. Currently known SC PGAs typically operate using either a sample and hold scheme or a sample and track (with a one to one gain) scheme. However, by implementing a double-sampling with partial tracking scheme (with a partial gain), the sampling capacitors can be smaller in size in which the power requirements for the amplifier can be reduced, as compared to using one of the currently known SC PGAs.

Referring to FIG. 4, for the sample phase of PGA 104, φs is asserted such that switches 402, 408, 416, 422, 428, and 434 are closed and the remaining switches open. In this manner, the sample capacitors are coupled to the input (e.g. $C_{sample}$ 410 is coupled to INP via closed switch 402, and $C_{sample}$ 412 to INM via closed switch 408), and the partial tracking capacitors are coupled to ground (e.g. $C_{pt}$ 420 is coupled between $C_{sample}$ 410 and ground via closed switch 422, and $C_{pt}$ 426 is coupled between $C_{sample}$ 412 and ground via closed switch 434). (Note that this ground may be an analog ground, or alternatively, this ground can be a positive power supply, negative power supply, or common ground.) As part of the CDS scheme, capacitors 420 and 426 store the offset, low-frequency noise, and finite gain errors of the amplifier during this phase. The sample capacitors $C_{sample}$ 410 and $C_{sample}$ 412 are differentially charged with the input signal Vin, in which Vin is the voltage at INP (Vinp) minus the voltage at INM (Vinm). In the sample phase, capacitor 418 is coupled between the first input of amplifier 400 (circuit node 438) via closed switch 416 and the first output of amplifier 400 (circuit node 442). Similarly, capacitor 436 is coupled between the second input of amplifier 400 (circuit node 440) via closed switch 428 and the second output of amplifier 400 (circuit node 444). As part of the CDS scheme, capacitors 418 and 436 hold the output voltage.

For the partial tracking phase of PGA 104, φpt is asserted such that switches 404, 406, 414, 424, 432, and 430 are now closed and the remaining switches open. In this manner, the sample capacitors are inversely coupled to the inputs, INP and INM, and the partial tracking capacitors (also referred to as hold capacitors) are coupled to the outputs, OUTP and OUTM. That is, rather than disconnecting $C_{sample}$ 410 and $C_{sample}$ 412 from the inputs INP and INM, as would be done in a PGA using a sample and hold scheme, $C_{sample}$ 410 is instead coupled to INM via closed switch 404 and $C_{sample}$ 412 is instead coupled to INP via closed switch 406. $C_{pt}$ 420 is coupled between circuit node 438 and OUTP (at circuit node 442) via closed switch 424, and $C_{pt}$ 426 is coupled between circuit node 440 and OUTM (at circuit node 444) via closed switch 432. In this configuration, capacitors 420 and 426 subtract the amplifier errors stored during the sample phase. Capacitors 418 and 436 are now coupled to ground via closed switches 414 and 430. (As described above, this ground can be an analog ground, but can also be a positive supply voltage, negative supply voltage, or common ground.) In this configuration, capacitors 418 and 436 sample the output voltage as part of the CDS scheme.

In the partial tracking phase, the sample capacitors $C_{sample}$ 410 and $C_{sample}$ 412 are differentially charged with the inversed input signal −Vin. The change of the charge is transferred to the partial tracking capacitors (e.g. to $C_{pt}$ 420 from $C_{sample}$ 410 and to $C_{pt}$ 426 from $C_{sample}$ 412) and generates the output voltage Vout in which Vout is the voltage at OUTP (Voutp) minus the voltage at OUTM (Voutm). Therefore, Vout can be represented as Vout=(Vin−(−Vin))*$C_{sample}/C_{pt}$=Vin*(2$C_{sample}/C_{pt}$). If the input signal changes by ΔVin during the partial tracking phase, the charge on the sample capacitors will change by ΔVin*$C_{sample}$, and this portion of charge will also be transferred to the partial tracking capacitors, generating the output voltage as $V_{out}=V_{in}*(2C_{sample}/C_{pt}+\Delta V_{in}*C_{sample}/C_{pt})$. This is a partial tracking because, for example, when the gain of PGA 104 is one, $C_{sample}$ equals a fraction of $C_{pt}$, e.g., $C_{sample}=0.5*C_{pt}$, causing the output Vout to track at a fraction of $\Delta V_{in}$, e.g. $0.5*\Delta V_{in}$. Therefore, note that the partial tracking phase provides amplified signals with a gain based on a ratio of the sample and partial tracking capacitors. In the illustrated embodiment, each of the sample and partial tracking capacitors are implemented as variable capacitors which can be set to the desired capacitances to achieve the desired gain.

With the illustrated SC PGA 104 with partial tracking, note that the smaller sampling capacitors due to double-sampling saves cost by requiring less circuit area for a given noise level as compared to currently known sample and hold and sample and track PGAs. Also, there is no additional circuitry to adjust gain in the tracking phase to match the overall PGA gain. However, through the use of partial tracking and the smaller sampling capacitors, the output of PGA 104 can include more distortion as compared to currently known PGAs. However this distortion, with proper selection of ADC sampling rate relative to PGA sampling rate, can be force to higher out-of-band frequencies which, as will be described below, can be filtered out by ADC circuitry 106.

Figure 2:
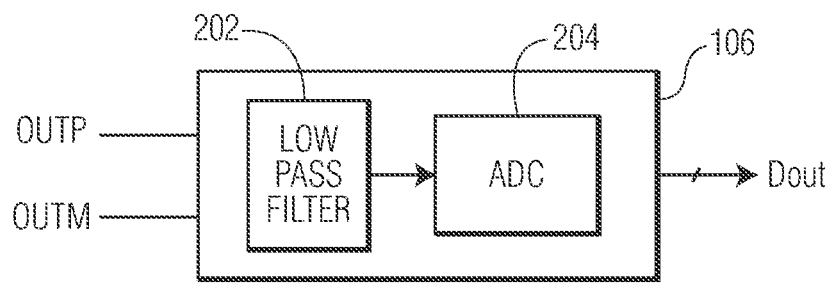
FIG. 2 illustrates, in block diagram form, a more detailed view of the analog-to-digital converter (ADC) circuitry of FIG. 1, in accordance with one embodiment of the present invention.
Figure 3:
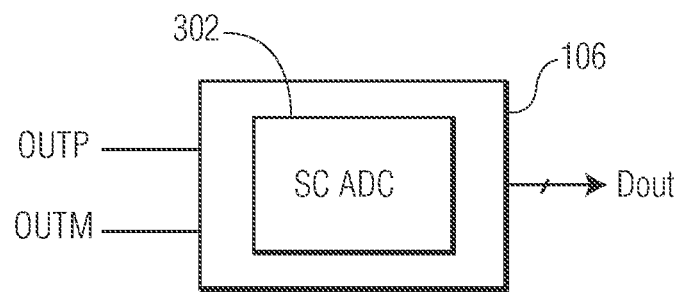
FIG. 3 illustrates, in block diagram form, a more detailed view of the analog-to-digital converter (ADC) circuitry of FIG. 1, in accordance with one embodiment of the present invention.

FIGS. 2 and 3 illustrate, in block diagram form, embodiments of ADC circuitry 106. In one embodiment, as described above, PGA 104, in amplifying the received differential signal, introduces high-frequency distortion in the signal path. This distortion is therefore removed by ADC circuitry 106. In one embodiment, such as illustrated in FIG. 2, ADC circuitry 106 can be implemented with an ADC 204 in combination with a low pass filter 202. In this example, low pass filter 202 removes the high-frequency distortion, resulting in a higher accuracy conversion to a digital signal by ADC 204, which can be implemented with any type of ADC.

In one embodiment, such as illustrated in FIG. 3, ADC circuitry 106 can be implemented by a sigma delta (SD) ADC 302. An SD ADC, as known in the art, typically includes a sigma-delta modulator in series with a digital filter. The modulator converts the analog input signal into a pulse wave representation. The modulator produces a noise-shaped output. In one embodiment, a second-order modulator is used to further shape any noise into the higher frequencies. The number of integrators, and thus feedback loops, in the modulator indicates the order of the SD ADC. The digital filter is already mandatory in a SD ADC to remove the out-of-band noise which has been shaped from lower frequencies to higher frequencies. This digital filter will also remove the high frequency distortion caused by the partial tracking. In the illustrated embodiment, SD ADC 302 has a high input sampling rate which is greater than the sampling rate of PGA 104. A decimator may also be used as part of the digital filter to down-sample the output of the low pass filter in order to slow down the output data rate. Note that for this embodiment, any known SD ADC circuit may be used to implement ADC circuitry 106.

Figure 7:
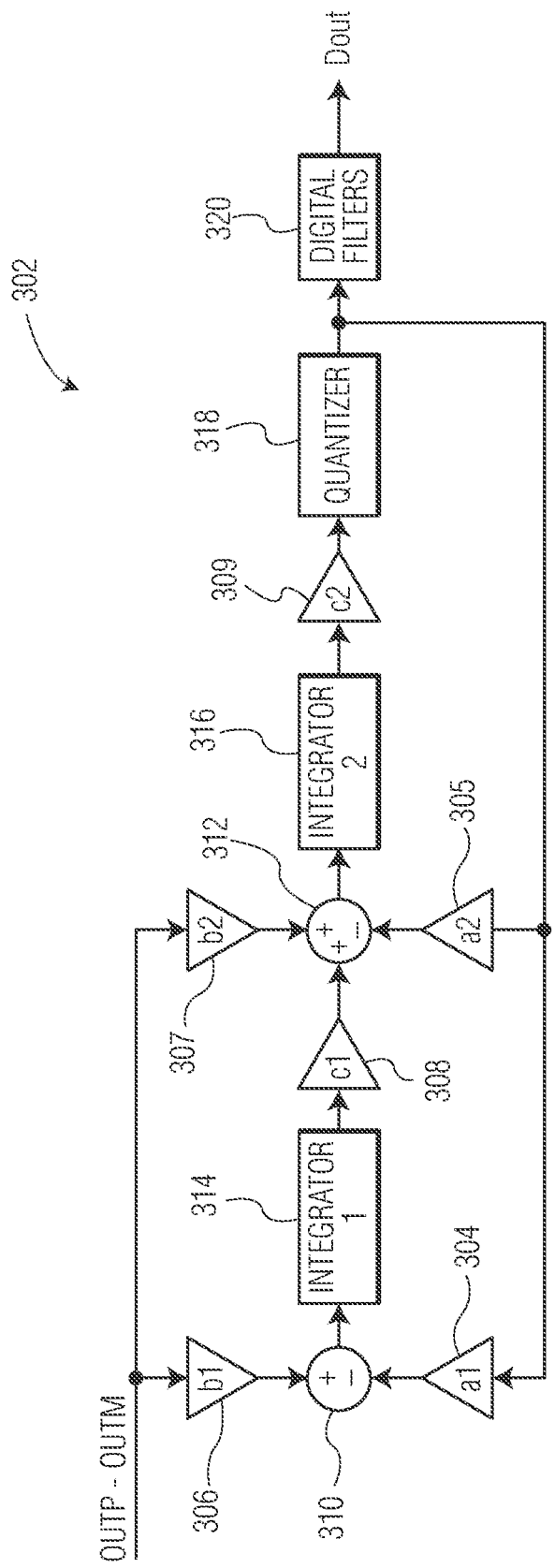
FIG. 7 illustrates, in block diagram form, a more detailed view of the ADC circuitry of FIG. 3, in accordance with one embodiment of the present invention.

FIG. 7 illustrates, in block diagram form, a more detailed view of one embodiment of SD ADC 302 (implemented as a second-order SD ADC), including coefficients 304-307, summing nodes 310, 312, and 309, integrators 314 and 316, a quantizer 318, and digital filters 320. Coefficients 304-307 scale the corresponding input or output signal. SD ADC 302 receives OUTP–OUTM as an input, an provides Dout as an output. Summing node 310 receives b1*(OUTP–OUTM) at a summing input and a1*(the output of quantizer 318)) at a subtractive input. Summing node 310 provides its result to integrator 314 (also referred to as integrator 1). The output of integrator 314 is scaled by c1 and is provided to a first summing input of summing node 312. Summing node 312 receives b2*(OUTP–OUTM) at a second summing input and a2*(the output of quantizer 318) at a subtractive input. Summing node 312 provides its result to integrator 316 (also referred to as integrator 2). The output of integrator 316 is scaled by c2 and provided to quantizer 318. The output of quantizer 318 is fed back to coefficients 304 and 305, and is also provided to digital filters 320, and digital filters 320 provides Dout. Coefficients 304-307, summing nodes 310 and 312, integrators 314 and 316, and quantizer 318 implement a second order modulator (due to the two integrators/feedback loops) which provides a noise-shaped output to digital filters 320. As discussed above with respect to FIG. 3, digital filters 320 includes a low pass filter to remove the out-of-band noise which has been shaped to higher frequencies by the modulator, and digital filters 320 may also include a decimator.

Figure 5:
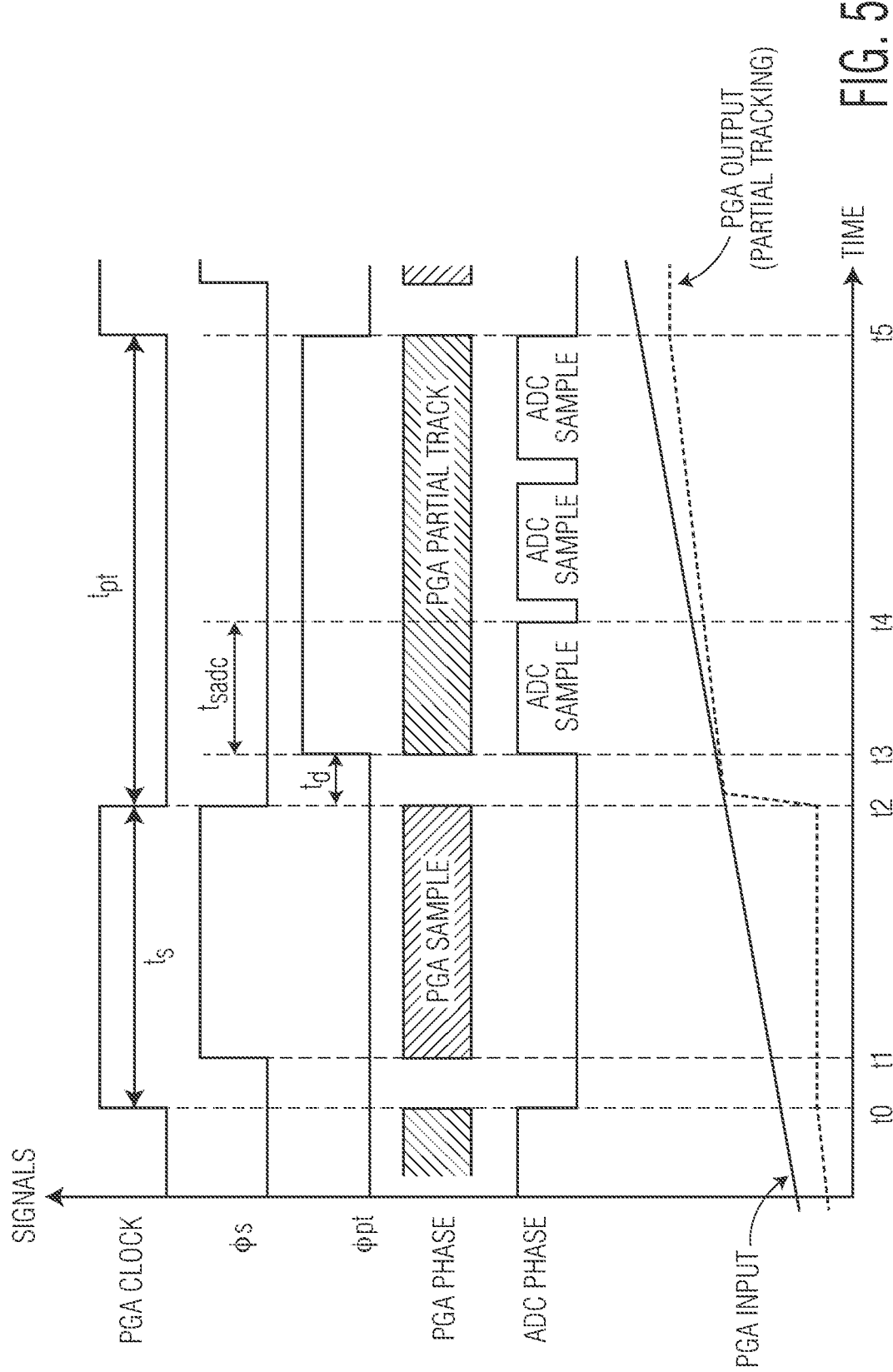
FIG. 5 illustrates, in timing diagram form, various signals of the system of FIG. 1, in accordance with one embodiment of the present invention.

FIG. 5 illustrates a timing diagram for various signals of system 100, in accordance with one embodiment of the present invention. Sample and partial tracking phases of PGA 104 are generated based on the PGA clock received, for example, by PGA control circuit 450. The sample phase, during which φs is asserted, occurs during one phase of the PGA clock cycle (the high phase in the illustrated example, corresponding to ts between time t0 and time t2), and the partial tracking phase, during which φpt is asserted, occurs during the other phase of the PGA clock cycle (the low phase in the illustrated example, corresponding to tpt between time t2 and time t5). In one embodiment, ts<tpt. As illustrated in FIG. 5, the PGA sample phase corresponds to φs being asserted and the partial tracking phase corresponds to φpt being asserted. In one example, each of the PGA partial tracking phase and the PGA sampling phase are delayed with respect to the edge of the PGA clock. For example, φs is asserted at time t1, which occurs at a delay after time t0, and φpt is asserted at a time t3 which occurs at a delay time (td) after time t2.

During the PGA sample phase of PGA 104, ADC circuitry 106 is disabled, i.e. is not performing sampling and conversions. For example, the sample phases of ADC circuitry 106 only occur during the partial tracking phase of PGA 104 (during the time period tpt, specifically during the time between t3 and t5). In the illustrated embodiment, 3 ADC sample phases are illustrated for ADC circuitry 106, however, there can be more sample phases, such as, for example, 8 sample phases. Therefore, it can be seen that the sampling rate of ADC circuitry 106 is greater than the sampling rate of PGA 104 (e.g. 3 to 1 in the illustrated example).

Also illustrated in FIG. 5 is the PGA input signal, corresponding to $V_{in}=V_{inp}-V_{inm}$, and the PGA output signal, corresponding to $V_{out}=V_{outp}-V_{outm}$ (utilizing partial tracking as described above). During the PGA sample phase, Vout holds steady, until the end of the sample phase into the partial tracking phase where Vout tracks Vin with a partial gain.

Figure 6:
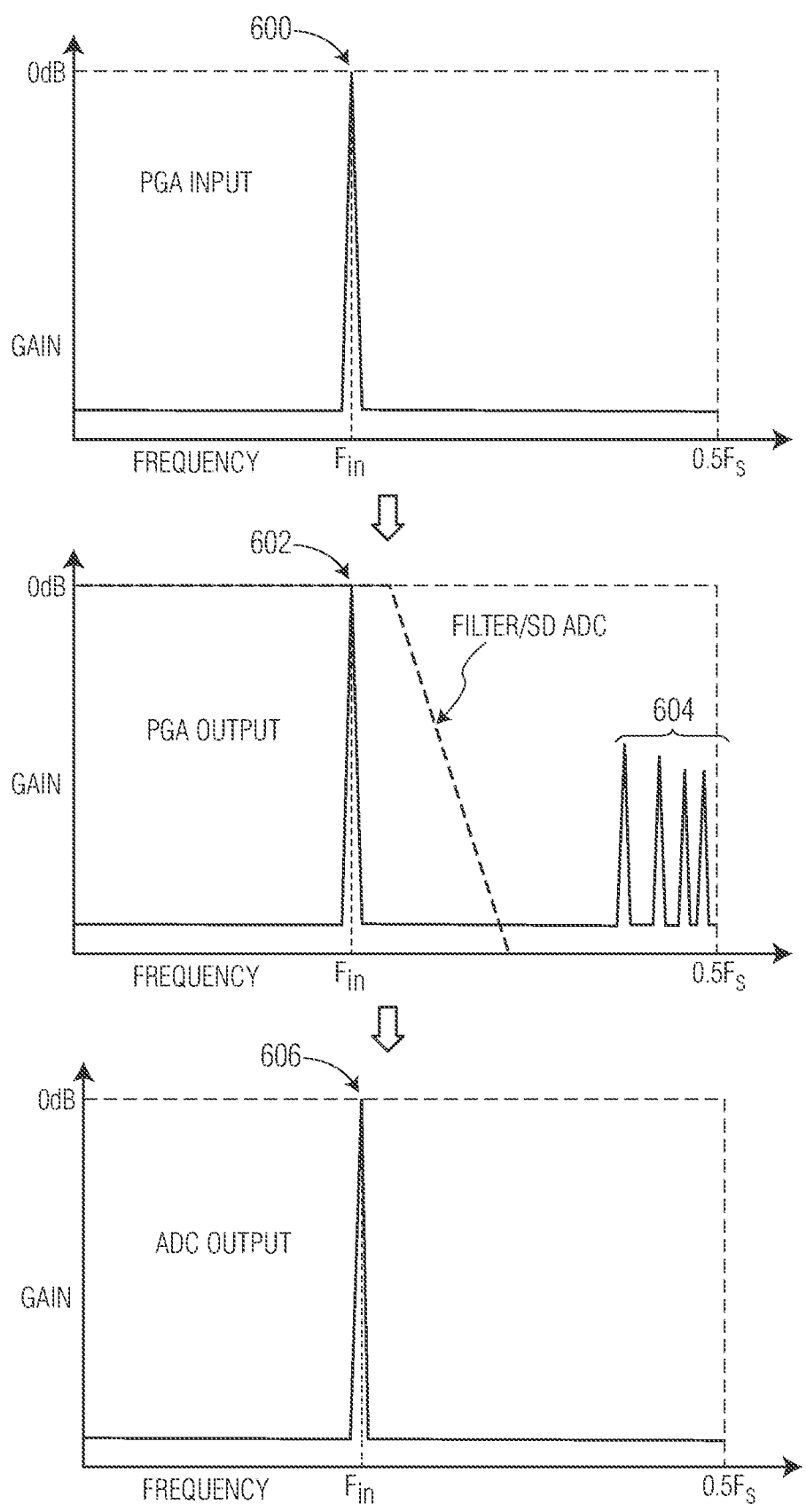
FIG. 6 illustrates an example frequency domain input and outputs of the system of FIG. 1.

FIG. 6 illustrates various frequency domain graphs for system 100 in accordance with one embodiment of the present invention. The first graph corresponds to Vin of PGA 104 and includes a fundamental frequency component 600 at frequency, Fin, which is the input frequency. The second graph corresponds to Vout of PGA 104 and includes a frequency component 602 at the frequency Fin but also includes frequency components 604 occurring in the higher frequencies of the frequency domain. These frequency components correspond to the distortion introduced by PGA 104, and their frequencies are based on the number of ADC samples per PGA sample (e.g. F(N)=k*(Fs/N)+/−Fin, in which N is the number of ADC samples per PGA sample, k=positive integers, and Fs is the effective ADC sample frequency N/(ts+tpt)). However, ADC circuitry 106 (either due to a low pass filter such as in FIG. 2 or due to the digital filter of an SD ADC such as in FIG. 3) filters out, i.e. removes, these distortion components, resulting in the third graph corresponding to the ADC output. This graph includes a fundamental frequency component 606 at frequency Fin, but without the distortion components. In this manner, the high frequency distortion introduced by the partial tracking scheme of PGA 104 is addressed by the ADC circuitry.

Therefore, it can be understood how cost (circuit area) and power can be saved in an analog front-end circuit through the use of a sample and partial tracking PGA, while maintaining accuracy through the use of an SD ADC or other ADCs in combination with a low pass filter. In this manner, an analog front-end circuitry is capable of converting low frequency and low amplitude signals to high resolution digital signals while saving cost and power.

The terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Each signal described herein may be designed as positive or negative logic, where negative logic can be indicated by a bar over the signal name or an asterix (*) following the name. In the case of a negative logic signal, the signal is active low where the logically true state corresponds to a logic level zero. In the case of a positive logic signal, the signal is active high where the logically true state corresponds to a logic level one. Note that any of the signals described herein can be designed as either negative or positive logic signals. Therefore, in alternate embodiments, those signals described as positive logic signals may be implemented as negative logic signals, and those signals described as negative logic signals may be implemented as positive logic signals.

Because the apparatus implementing the present invention is, for the most part, composed of electronic components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Some of the above embodiments, as applicable, may be implemented using a variety of different information processing systems. For example, although FIG. 1 and the discussion thereof describe an exemplary information processing architecture, this exemplary architecture is presented merely to provide a useful reference in discussing various aspects of the invention. Of course, the description of the architecture has been simplified for purposes of discussion, and it is just one of many different types of appropriate architectures that may be used in accordance with the invention. Those skilled in the art will recognize that the boundaries between logic blocks are merely illustrative and that alternative embodiments may merge logic blocks or circuit elements or impose an alternate decomposition of functionality upon various logic blocks or circuit elements.

Furthermore, those skilled in the art will recognize that boundaries between the functionality of the above described operations merely illustrative. The functionality of multiple operations may be combined into a single operation, and/or the functionality of a single operation may be distributed in additional operations. Moreover, alternative embodiments may include multiple instances of a particular operation, and the order of operations may be altered in various other embodiments.

Although the invention is described herein with reference to specific embodiments, various modifications and changes can be made without departing from the scope of the present invention as set forth in the claims below. For example, analog front-end circuit 110 may be used in a variety of applications, and is not limited to receiving and processing signals from sensors only. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

The term "coupled," as used herein, is not intended to be limited to a direct coupling or a mechanical coupling.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles.

Unless stated otherwise, terms such as "first" and "second" are used to arbitrarily distinguish between the elements such terms describe. Thus, these terms are not necessarily intended to indicate temporal or other prioritization of such elements.

The following are various embodiments of the present invention.

In one embodiment, a sensor system includes an amplifier having a first input, a second input, a first output, and a second output; a first sampling capacitor coupled between a first set of switches and the first input of the amplifier, the first set of switches operable to couple the first sampling capacitor to an output of a sensor during a sampling phase and to a reference voltage during a partial tracking phase; a second sampling capacitor coupled between a second set of switches and the second input of the amplifier, the second set of switches operable to couple the second sampling capacitor to the reference voltage during the sampling phase and to the output of the sensor during the partial tracking phase; and an analog to digital converter (ADC) circuit with a low pass transfer function having an input coupled to the output of the amplifier. In one aspect, the ADC converter circuit is a sigma-delta converter circuit. In a further aspect, during the partial tracking phase, the ADC converter circuit is sampling the output of the amplifier at a frequency that is higher than the first and second sampling capacitor sampling frequency. In another aspect of the above embodiment, the first sampling capacitor is coupled to a first output of a sensor during the sampling phase, and during the partial tracking phase, the first sampling capacitor is coupled to one of a power supply voltage and a second output of the sensor. In a further aspect, the second sampling capacitor is coupled to the one of the power supply voltage and the second output of the sensor during the sampling phase, and the second sampling capacitor is coupled to the first output of the sensor during the partial tracking phase. In yet a further aspect, the sensor system further includes a third sampling capacitor having a first terminal coupled to the first output of the amplifier and a second terminal coupled to the first input of the amplifier during the sampling phase and to a second power supply voltage during the partial tracking phase. In yet a further aspect, the sensor system further includes a fourth sampling capacitor having a first terminal coupled to the second output of the amplifier and a second terminal coupled to the second output of the amplifier during sampling phase and the second power supply voltage during the partial tracking phase. In yet an even further aspect, the third and fourth sampling capacitors are coupled to the second power supply voltage during the partial tracking phase to implement a correlated double sampling function. In yet an even further aspect, the first, second, third and fourth sampling capacitors are coupled to the output of the amplifier with non-overlapping clock signals during one of a transition from sampling phase to partial tracking phase, and a transition from partial tracking phase to sampling phase.

In another embodiment, a sensing device includes a signal processing unit; an analog to digital converter with sampling frequency higher than a first sampling capacitor sampling frequency, the analog to digital converter including a low pass filter transfer function; an analog front end circuit including: during a sampling phase, a first terminal of a first sampling capacitor is connected to an analog input signal, a first terminal of a second sampling capacitor is connected to a reference signal, and first and second hold capacitors are connected to ground; and during a partial tracking phase, the first terminal of the first sampling capacitor is connected to the reference voltage, the first terminal of the second sampling capacitor is connected to the analog input signal, the first hold capacitor is connected to a first output of an amplifier and the second hold capacitor is connected to a second output of the amplifier, and a second terminal of the first sampling capacitor is coupled to a first input of the amplifier and a second terminal of the second sampling capacitor is coupled to a second input of the amplifier.

In yet another embodiment, a method of operating an analog front end circuit includes during a sampling phase: connecting a first terminal of a first sampling capacitor to an analog input signal and a first terminal of a second sampling capacitor to a first reference voltage, and connecting first and second hold capacitors to one of a first power supply voltage and a second reference voltage; and during a partial tracking phase: connecting the first terminal of the first sampling capacitor to the first reference voltage and the first terminal of the second sampling capacitor to the analog input signal, connecting a first terminal of the first hold capacitor to a first output of an amplifier and a first terminal of the second hold capacitor to a second output of the amplifier; and coupling an analog to digital converter to the first and second outputs of the amplifier during the partial tracking phase, and decoupling the analog to digital converter from the first and second outputs of the amplifier during the sampling phase, wherein a second terminal of the first sampling capacitor is coupled to a first input of the amplifier and a second terminal of the second sampling capacitor is coupled to a second input of the amplifier. In one aspect, the first sampling capacitor is coupled to a first output of a sensor during the sampling phase, and during the partial tracking phase, the first sampling capacitor is coupled to one of a second power supply voltage and a second output of the sensor. In a further aspect, the second sampling capacitor is coupled to one of the second power supply voltage or the second output of the sensor during the sampling phase, and the second sampling capacitor is coupled to the first output of the sensor during the partial tracking phase. In another aspect of the yet another embodiment, the method further includes low pass filtering the first and second output of the amplifier in a low pass filter circuit; and converting an output from the low pass filter circuit from an analog signal to a digital signal using an analog to digital converter. In another aspect, the method further includes using a sigma delta analog to digital converter (ADC) circuit to convert the first and second outputs of the amplifier from analog signals to a digital signal. In yet another aspect of the yet another embodiment, the method further includes, during the sampling phase: coupling a third capacitor between the first input of the amplifier and the first output of the amplifier; and coupling a fourth capacitor between the second input of the amplifier and the second output of the amplifier. In a further aspect, the method further includes, during the partial tracking phase, coupling the third and fourth capacitors to a second power supply voltage to perform correlated double sampling. In another further aspect, the amplifier is coupled to the analog input signal during the partial tracking phase and the output of the amplifier tracks the analog input signal with a gain that depends on a ratio of one of the first sampling capacitor and the first hold capacitor, and the second sampling capacitor and the second hold capacitor. In another further aspect, the method further includes removing distortion in the first and second output of the gain amplifier using one of a low pass filter circuit and a sigma delta analog to digital converter. In another aspect, during the partial tracking phase, the ADC circuit samples the first and second outputs of the amplifier at a frequency that is higher than a sampling frequency of the first and second sampling capacitors.

What is claimed is:
1. A sensor system comprising:
an amplifier having a first input, a second input, a first output, and a second output;
a first sampling capacitor coupled between a first set of switches and the first input of the amplifier, the first set of switches operable to couple the first sampling capacitor to an output of a sensor during a sampling phase and to a reference voltage during a partial tracking phase;
a second sampling capacitor coupled between a second set of switches and the second input of the amplifier, the second set of switches operable to couple the second sampling capacitor to the reference voltage during the sampling phase and to the output of the sensor during the partial tracking phase; and
an analog to digital converter (ADC) circuit with a low pass transfer function having an input coupled to the output of the amplifier.
2. The sensor system of claim 1, wherein the ADC converter circuit is a sigma-delta converter circuit.

3. The sensor system of claim 2, wherein, during the partial tracking phase, the ADC converter circuit is sampling the output of the amplifier at a frequency that is higher than the first and second sampling capacitor sampling frequency.

4. The sensor system of claim 1 wherein the first sampling capacitor is coupled to a first output of a sensor during the sampling phase, and during the partial tracking phase, the first sampling capacitor is coupled to one of a power supply voltage and a second output of the sensor.

5. The sensor system of claim 4 wherein the second sampling capacitor is coupled to the one of the power supply voltage and the second output of the sensor during the sampling phase, and the second sampling capacitor is coupled to the first output of the sensor during the partial tracking phase.

6. The sensor system of claim 5, further comprising:
a third sampling capacitor having a first terminal coupled to the first output of the amplifier and a second terminal coupled to the first input of the amplifier during the sampling phase and to a second power supply voltage during the partial tracking phase.

7. The sensor system of claim 6, further comprising:
a fourth sampling capacitor having a first terminal coupled to the second output of the amplifier and a second terminal coupled to the second input of the amplifier during sampling phase and the second power supply voltage during the partial tracking phase.

8. The sensor system of claim 7, wherein the third and fourth sampling capacitors are coupled to the second power supply voltage during the partial tracking phase to implement a correlated double sampling function.

9. The sensor system of claim 8, wherein the first, second, third and fourth sampling capacitors are coupled to the output of the amplifier with non-overlapping clock signals during one of a transition from sampling phase to partial tracking phase, and a transition from partial tracking phase to sampling phase.

10. A sensing device comprising:
a signal processing unit;
an analog to digital converter with sampling frequency higher than a first sampling capacitor sampling frequency, the analog to digital converter including a low pass filter transfer function;
an analog front end circuit including:
during a sampling phase, a first terminal of a first sampling capacitor is connected to an analog input signal, a first terminal of a second sampling capacitor is connected to a reference signal, and first and second hold capacitors are connected to ground;
during a partial tracking phase,
the first terminal of the first sampling capacitor is connected to the reference voltage,
the first terminal of the second sampling capacitor is connected to the analog input signal,
the first hold capacitor is connected to a first output of an amplifier and the second hold capacitor is connected to a second output of the amplifier, and
a second terminal of the first sampling capacitor is coupled to a first input of the amplifier and a second terminal of the second sampling capacitor is coupled to a second input of the amplifier.

11. A method of operating an analog front end circuit, the method comprising:
during a sampling phase:
connecting a first terminal of a first sampling capacitor to an analog input signal and a first terminal of a second sampling capacitor to a first reference voltage;
connecting first and second hold capacitors to one of a first power supply voltage and a second reference voltage; and
during a partial tracking phase:
connecting the first terminal of the first sampling capacitor to the first reference voltage and the first terminal of the second sampling capacitor to the analog input signal;
connecting a first terminal of the first hold capacitor to a first output of an amplifier and a first terminal of the second hold capacitor to a second output of the amplifier; and
coupling an analog to digital converter to the first and second outputs of the amplifier during the partial tracking phase, and decoupling the analog to digital converter from the first and second outputs of the amplifier during the sampling phase;
wherein a second terminal of the first sampling capacitor is coupled to a first input of the amplifier and a second terminal of the second sampling capacitor is coupled to a second input of the amplifier.

12. The method of claim 11 wherein the first sampling capacitor is coupled to a first output of a sensor during the sampling phase, and during the partial tracking phase, the first sampling capacitor is coupled to one of a second power supply voltage and a second output of the sensor.

13. The method of claim 12 wherein the second sampling capacitor is coupled to one of the second power supply voltage or the second output of the sensor during the sampling phase, and the second sampling capacitor is coupled to the first output of the sensor during the partial tracking phase.

14. The method of claim 11, further comprising:
low pass filtering the first and second output of the amplifier in a low pass filter circuit; and
converting an output from the low pass filter circuit from an analog signal to a digital signal using an analog to digital converter.

15. The method of claim 11, further comprising:
using a sigma delta analog to digital converter (ADC) circuit to convert the first and second outputs of the amplifier from analog signals to a digital signal.

16. The method of claim 11, further comprising:
during the sampling phase:
coupling a third capacitor between the first input of the amplifier and the first output of the amplifier; and
coupling a fourth capacitor between the second input of the amplifier and the second output of the amplifier.

17. The method of claim 16, further comprising:
during the partial tracking phase:
coupling the third and fourth capacitors to a second power supply voltage to perform correlated double sampling.

18. The method of claim 16, wherein the amplifier is coupled to the analog input signal during the partial tracking phase and the output of the amplifier tracks the analog input signal with a gain that depends on a ratio of one of the first sampling capacitor and the first hold capacitor, and the second sampling capacitor and the second hold capacitor.

19. The method of claim 17, further comprising:
removing distortion in the first and second output of the gain amplifier using one of a low pass filter circuit and a sigma delta analog to digital converter.

20. The method of claim 15, wherein, during the partial tracking phase, the ADC circuit samples the first and second outputs of the amplifier at a frequency that is higher than a sampling frequency of the first and second sampling capacitors.

* * * * *